United States Patent [19]

Scherkenbeck et al.

[11] Patent Number: 5,140,035
[45] Date of Patent: Aug. 18, 1992

[54] FUNGICIDAL TRIAZOLYMETHYL-CYCLOPROPYL DERIVATIVES

[75] Inventors: Jürgen Scherkenbeck, Leverkusen; Klaus Stroech, Solingen; Burghard Fugmann, Wuelfrath; Stefan Dutzmann, Duesseldorf, all of Fed. Rep. of Germany

[73] Assignee: Bayer Aktiengesellschaft, Leverkusen, Fed. Rep. of Germany

[21] Appl. No.: 629,284

[22] Filed: Dec. 17, 1990

[30] Foreign Application Priority Data

Dec. 21, 1989 [DE] Fed. Rep. of Germany ....... 3942417

[51] Int. Cl.$^5$ ................. A01N 43/653; C07D 249/08
[52] U.S. Cl. ................................... 514/383; 514/184; 548/101; 548/268.6
[58] Field of Search ............... 548/101, 268.6; 514/184, 383

[56] References Cited

U.S. PATENT DOCUMENTS

| | | | |
|---|---|---|---|
| 4,548,945 | 10/1985 | Holmwood et al. | 548/267.8 |
| 4,870,088 | 9/1989 | Blume et al. | 548/267.8 |
| 4,913,727 | 4/1990 | Stoech et al. | 71/92 |
| 4,921,528 | 5/1990 | Böckmann et al. | 71/92 |
| 4,925,482 | 5/1990 | Stroech et al. | 548/267.8 |

*Primary Examiner*—Patricia L. Morris
*Attorney, Agent, or Firm*—Sprung Horn Kramer & Woods

[57] ABSTRACT

Fungicidal triazolylmethyl-cyclopropyl derivatives of the formula

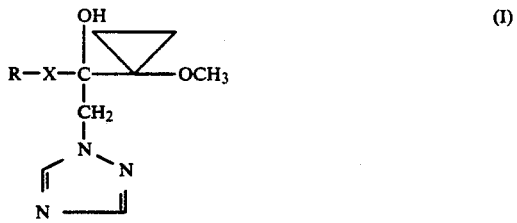

in which
R represents a radical of the formula

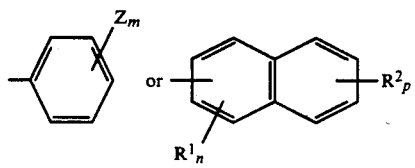

in which
Z represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, phenyl which is optionally substituted by at least one of alkyl having 1 or 2 carbon atoms and halogen, or represents phenoxy which is optionally substituted by at least one of alkyl having 1 or 2 carbon atoms and halogen, and
m represents the numbers 0, 1, 2 or 3,
$R^1$ represents halogen, alkyl having 1 to 4 carbon atoms or alkoxy having 1 to 4 carbon atoms,
n represents the numbers 0, 1 or 2,
$R^2$ represents halogen, alkyl having 1 to 4 carbon atoms or alkoxy having 1 to 4 carbon atoms and
p represents the numbers 0, 1 or 2, and
X represents $CH_2$ or a direct bond,
and addition products thereof with acids and metal salts.

6 Claims, No Drawings

FUNGICIDAL TRIAZOLYMETHYL-CYCLOPROPYL DERIVATIVES

The present application relates to new triazolylmethyl-cyclopropyl derivatives, to a process for their preparation and to their use as fungicides.

It has already been disclosed that certain azolylmethyl-cyclopropyl derivatives have fungicidal properties (compare EP-OS (European Published Specification) 0,180,136 and EP-OS (European Published Specification) 0,297,345). Thus, for example, 1-(4-phenylphenyl)-1-(1-methylthio-cyclopropyl)-2-(1,2,4-triazol-1-yl)-ethan-1-ol, 1-(4-chlorophenyl)-1-(1-methylthio-cyclopropyl)-2-(1,2,4-triazol-1-yl)-ethan-1-ol, 1-(4-fluorophenyl)-1-(1-methylthio-cyclopropyl)-2-(1,2,4-triazol-1-yl)-ethan-1-ol and 1-(2,4-difluoro-phenyl)-1-(1-methylthio-cyclopropyl)-2-(1,2,4-triazol-1-yl)-ethan-1-ol can be employed for combating fungi. The activity of these substances is good; however, in some cases it leaves something to be desired at low application rates.

New triazolylmethyl-cyclopropyl derivatives of the formula

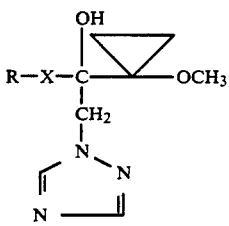
(I)

in which
R represents the radicals of the formulae

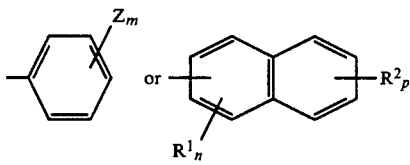

in which
Z represents halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, phenyl which is optionally substituted by alkyl having 1 to 2 carbon atoms and/or halogen or phenoxy which is optionally substituted by alkyl having 1 or 2 carbon atoms and/or halogen and
m represents the numbers 0, 1, 2 or 3,
$R^1$ represents halogen, alkyl having 1 to 4 carbon atoms or alkoxy having 1 to 4 carbon atoms,
n represents the numbers 0, 1 or 2,
$R^2$ represents halogen, alkyl having 1 to 4 carbon atoms or alkoxy having 1 to 4 carbon atoms and
p represents the numbers 0, 1 or 2, and
X represents $CH_2$ or a direct bond, and their acid addition salts and metal salt complexes have now been found.

It was furthermore been found that triazolylmethyl-cyclopropyl derivatives of the formula (I) and their acid addition salts and metal salt complexes are obtained when oxiranes of the formula

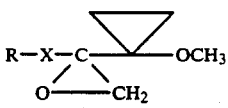
(II)

in which
R and X have the abovementioned meanings, are reacted with 1,2,4-triazole of the formula

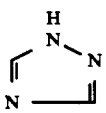
(III)

if appropriate in the presence of an acid-binding agent and in the presence of a diluent, and, if appropriate, an acid or a metal salt is subsequently added to the compounds of the formula (I) thus obtained.

Finally, it has been found that the new triazolylmethyl-cyclopropyl derivatives of the formula (I) and their acid addition salts and metal salt complexes have very good fungicidal properties.

The substances according to the invention contain an asymmetrically substituted carbon atom. They can therefore be obtained in optical isomer forms. The present invention relates both to the individual isomers and to their mixtures.

Surprisingly, the substances according to the invention have a better fungicidal activity than 1-(4-phenylphenyl)-1-(1-methylthio-cyclopropyl)-2-(1,2,4-triazol-1-yl)-ethan-1-ol, 1-(4-chloro-phenyl)-1-(1-methylthio-cyclopropyl)-2-(1,2,4-triazol-1-yl)-ethan-1-ol, 1-(4-fluoro-phenyl)-1-(1-methylthio-cyclopropyl)-2-(1,2,4-triazol-1-yl)-ethan-1-ol and 1-(2,4-difluorophenyl)-1-(1-methylthio-cyclopropyl)-2-(1,2,4-triazol-1-yl)-ethan-1-ol, which are constitutionally similar, previously known active compounds of the same type of action.

Formula (I) provides a general definition of the triazolylmethyl-cyclopropyl derivatives according to the invention. Preferably, in this formula
R represents the radicals of the formulae

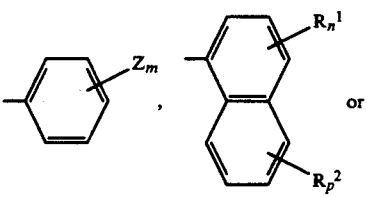

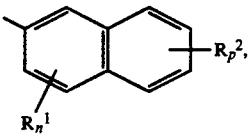

in which
Z represents fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl or phenoxy which is optionally substituted by fluorine, chlorine and/or methyl, m represents the numbers 0, 1, 2 or 3, $R^1$ represents fluorine, chlorine, methyl, ethyl, methoxy or ethoxy, m represents the numbers 0, 1 or 2, $R^2$ represents fluorine, chlorine, methyl, ethyl, methoxy or ethoxy and p represents the numbers 0, 1 or 2, and X represents $CH_2$ or a direct bond.

If m represents the numbers 2 or 3, the radicals represented by Z may be identical or different.

The radicals represented by $R^1$ or $R^2$ may also be identical or different if n or p represents 2.

Preferred substances according to the invention are also addition products of acids and those triazolylmethyl-cyclopropyl derivatives of the formula (I) in which R and X have the meanings which have already been mentioned as preferred for these radicals.

The acids which can be adducted preferably include hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

Additionally preferred compounds according to the invention are addition products of salts of metals of main groups II to IV and sub-groups I and II as well as IV to VIII of the periodic table of the elements and those triazolylmethyl-cycylopropyl derivatives of the formula (I) in which R and X have the meanings which have already been mentioned as preferred for these radicals.

In this connection, salts of copper, zinc, manganese, magnesium, tin, iron and nickel are particularly preferred. Possible anions of these salts are those which are derived from those acids which lead to physiologically tolerable addition products.

Particularly preferred acids of this type are, in this connection, the hydrohalic acids, such as, for example, hydrochloric acid and hydrobromic acid, and furthermore phosphoric acid, nitric acid and sulphuric acid.

Examples of triazolylmethyl-cyclopropyl derivatives of the formula (I) which may be mentioned are the substances shown in the following table.

TABLE

| R | X |
|---|---|
| 2-Cl-C₆H₄ | CH₂ |
| 2-Cl-C₆H₄ | — |
| 2,4-Cl₂-C₆H₃ | CH₂ |
| 4-Cl-C₆H₄ | CH₂ |
| 2,4-Cl₂-C₆H₃ | — |
| 4-CF₃-C₆H₄ | CH₂ |
| 4-CF₃-C₆H₄ | — |
| 4-CF₃O-C₆H₄ | CH₂ |
| 4-CF₃O-C₆H₄ | — |
| 4-biphenyl | CH₂ |
| 4-phenoxyphenyl | — |
| 2-naphthyl | — |

TABLE-continued (I)

$$R-X-\underset{\underset{\underset{N\overset{\shortparallel}{\diagup}N}{\overset{|}{N}}}{\overset{|}{CH_2}}}{\overset{OH}{\overset{|}{C}}}-\triangle-OCH_3,$$

| R | X |
|---|---|
| F—⟨phenyl⟩— | — |
| F—⟨2-F-phenyl⟩— | CH₂ |

If 2-(4-fluoro-benzyl)-2-(1-methoxy-cyclopropyl)oxirane and 1,2,4-triazole are used as starting materials, the course of the process according to the invention can be illustrated by the following equation:

$$F-\text{⟨phenyl⟩}-CH_2-\underset{\underset{CH_2}{\overset{|}{O}}}{\overset{\triangle}{C}}-C-OCH_3 \quad + \quad HN\overset{N=}{\underset{N}{\diagup}} \longrightarrow$$

$$F-\text{⟨phenyl⟩}-CH_2-\underset{\underset{\underset{N\overset{\shortparallel}{\diagup}N}{\overset{|}{N}}}{\overset{|}{CH_2}}}{\overset{OH}{\overset{|}{C}}}-\triangle-OCH_3$$

Formula (II) provides a general definition of the oxiranes required as starting materials for the process according to the invention. In this formula, R and X preferably have those meanings which have already been mentioned as preferred for these radicals in connection with the description of the substances of the formula (I) according to the invention.

The oxiranes of the formula (II) have not previously been disclosed. They can be prepared by reacting cyclopropyl ketones of the formula $$R-X-\underset{\overset{\shortparallel}{O}}{C}-\triangle-OCH_3 \quad (IV)$$

in which
R and X have the abovementioned meanings, either
α) with dimethyloxosulphonium methylide of the formula $$(CH_3)_2 \overset{\delta\oplus}{S}O\overset{\delta\ominus}{CH_2} \quad (V)$$

or
β) with dimethylsulphonium methylide of the formula $$(CH_3)_2 \overset{\delta\oplus}{S} \overset{\delta\ominus}{CH_2} \quad (VI)$$

in the presence of a diluent.

The cyclopropyl ketones of the formula (IV) have also not previously been disclosed. They can be prepared by reacting N-methoxy-N-methyl-1-methoxy-cyclopropane-carboxamide of the formula $$\underset{CH_3}{\overset{CH_3O}{\diagdown}}N-\underset{\overset{\shortparallel}{O}}{C}-\triangle-OCH_3 \quad (VII)$$

either
γ) with Grignard compounds of the formula $$R-CH_2-MgX^1 \quad (VIII)$$

in which
R has the abovementioned meaning and
X¹ represents chlorine, bromine or iodine, in the presence of a diluent,
or
δ) with halogen compounds of the formula $$R-Hal \quad (IX)$$

in which
R has the abovementioned meaning and
Hal represents bromine or iodine, in the presence of a strong base and in the presence of a diluent.

N-Methoxy-N-methyl-1-methoxy-cyclopropane-carboxamide of the formula (VII) has also not previously been disclosed. It can be prepared by reacting 1-methoxy-cyclopropane-carbonyl chloride of the formula $$Cl-\underset{\overset{\shortparallel}{O}}{C}-\triangle-OCH_3 \quad (X)$$

with N,O-dimethyl-hydroxylamine hydrochloride of the formula $$\underset{CH_3}{\overset{CH_3O}{\diagdown}}NH \times HCl \quad (XI)$$

in the presence of an acid-binding agent and in the presence of a diluent.

1-Methoxy-cyclopropane-carbonyl chloride of the formula (X) has likewise not previously been described. It can be prepared by reacting 1-methoxy-cyclopropane-carboxylic acid of the formula $$HO-\underset{\overset{\shortparallel}{O}}{C}-\triangle-OCH_3 \quad (XII)$$

with thionyl chloride, if appropriate in the presence of an inert diluent, at temperatures between 0° C. and 100° C. Working-up is carried out by customary methods.

The compounds of the formulae (VII), (IX), (XI) and (XII) required as starting materials or reaction components in the above processes are known (compare J. Amer. Chem. Soc. 108, 2393 (1986)).

In the above process for the preparation of N-methoxy-N-methyl-1-methoxy-cyclopropane-carboxamide, suitable acid-binding agents are preferably tertiary aliphatic and aromatic amines, such as triethylamine, N,N-dimethyl-cyclohexyl-amino, N,N-dimethyl-benzylamine and pyridine, and additionally cyclic amines, such as 1,5-diaza-bicyclo-[4.3.0]-non-5-ene (DBN), 1,8-diaza-bicyclo[5.4.0]undec-7-ene (DBU) and 1,4-diaza-bicyclo[2.2.2]octane (DABCO).

Possible diluents in the above process for the preparation of N-methoxy-N-methyl-1-methoxy-cyclopropane-carboxamide of the formula (VII) are all inert organic solvents customary for reactions of this type. Those which can be preferably used are halogenated aliphatic hydrocarbons, such as dichloromethane, chloroform and carbon tetrachloride.

The reaction temperatures can be varied within a certain range in the above process for the preparation of N-methoxy-N-methyl-1-methoxy-cyclopropane-carboxamide of the formula (VII). In general, the reaction is carried out at temperatures between −10° C. and +80° C., preferably between 0° C. and +60° C.

In the above process for the preparation of N-methoxy-N-methyl-1-methoxy-cyclopropane-carboxamide of the formula (VII), the reaction is in general carried out under normal pressure, just as in the other processes described in this application.

In the above process for the preparation of N-methoxy-N-methyl-1-methoxy-cyclopropane-carboxamide of the formula (VII), an equivalent amount or alternatively an excess of acid-binding agent is employed per mole of 1-methoxy-cyclopropane-carbonyl chloride of the formula (X). Working-up is carried out by customary methods. In general, a procedure is used in which the reaction mixture is filtered and, if appropriate after previously diluting with a sparingly water-soluble organic solvent, washed with water, then dried and concentrated and the remaining residue is distilled.

In variant (δ) of the above process for the preparation of cyclopropyl ketones of the formula (IV), a suitable strong base is preferably n-butyllithium.

Possible diluents for carrying out variant (δ) of the above process for the preparation of cyclopropyl ketones of the formula (IV) are all inert organic solvents customary for reactions of this type. Those which can be preferably used are ethers, such as diethyl ether.

The reaction temperatures can be varied within a certain range when carrying out variant (δ) of the above process for the preparation of cyclopropyl ketones. In general, the reaction is carried out at temperatures between −80° C. and +40° C.

When carrying out variant (δ) of the above process for the preparation of cyclopropyl ketones of the formula (IV), an equivalent amount or alternatively an excess of halogen compound of the formula (IX) and also an equivalent amount or alternatively an excess of strong base are employed per mole of N-methoxy-N-methyl-1-methoxycyclopropane-carboxamide. Working-up is carried out by customary methods. In general, a procedure is used in which the reaction mixture, if appropriate after previously diluting with an organic solvent, is poured into ice-water, then extracted with a sparingly water-soluble organic solvent, and the combined organic phases are dried and then concentrated by stripping off the diluent under reduced pressure.

Possible diluents for carrying out varient (γ) of the above process for the preparation of cyclopropyl ketones of the formula (IV) are all inert organic solvents customary for reactions of this type. Those which can preferably be used are ethers, such as diethyl ether, tetrahydrofuran and dioxane.

The reaction temperatures can be varied within a certain range when carrying out variant (γ) of the above process for the preparation of cyclopropyl ketones of the formula (IV). In general, the reaction is carried out at temperatures between −80° C. and +50° C. preferably between −80° C. and 40° C.

When carrying out variant (γ) of the above process for the preparation of cyclopropyl ketones of the formula (IV), 1 to 1.5 moles of Grignard compound of the formula (VIII), which is expediently prepared immediately beforehand and further processed in situ, are in general employed per mole of N-methoxy-N-methyl-1-methoxy-cyclopropane-carboxamide of the formula (VII). Working-up is carried out by customary methods. In general, a procedure is used in which the mixture is first acidified and water is added, then the organic phase is separated off, washed and concentrated after drying.

The dimethyloxosulphonium methylide of the formula (V) required as a reaction component for carrying out variant (α) of the process for the preparation of oxiranes of the formula (II) is known (compare J. Am. Chem. Soc. 87, 1363–1364 (1965)). It is processed in the above reaction in a freshly prepared state, by generating it in situ by reaction of trimethyloxosulphonium iodide with sodium hydride or sodium amide, in particular with potassium tert.-butoxide of sodium methoxide, in the presence of a diluent.

The dimethylsulphonium methylide of the formula (VI) additionally possible as a reaction component for carrying out variant (β) of the process for the preparation of oxiranes of the formula (II) is also known (compare Heterocycles 8, 397 (1977)). It is also employed in the above reaction in a freshly prepared state by generating it in situ, for example from trimethylsulphonium halide or trimethylsulphonium methylsulphate, in the presence of a strong base, such as, for example, sodium hydride, sodium amide, sodium methoxide, potassium tert.-butoxide or potassium hydroxide, in the presence of a diluent, such as tert.-butanol or dimethyl sulphoxide.

Suitable diluents for carrying out the above process for the preparation of oxiranes of the formula (II) are inert organic solvents. Those which can preferably be used are alcohols, such as tert.-butanol, ethers, such as tetrahydrofuran or dioxane, furthermore aliphatic and aromatic hydrocarbons, such as benzene, toluene or xylene, and also strongly polar solvents, such as dimethyl sulphoxide.

The reaction temperatures can be varied within a relatively wide range when carrying out the above process for the preparation of oxiranes of the formula (II). In general, the reaction is carried out between 0° C. and 100° C., preferably between 10° C. and 60° C.

When carrying out the above process for the preparation of oxiranes of the formula (II), 1 to 3 moles of dimethyloxosulphonium methylide of the formula (V) or of dimethylsulphonium methylide of the formula (VI) are in general employed per mole of cyclopropyl ketone of the formula (IV). The oxiranes of the formula (II) are isolated by customary methods.

Suitable acid-binding agents for carrying out the process according to the invention are all customary inorganic and organic bases. Those which can preferably be used are alkali metal carbonates, such as sodium carbonate and potassium carbonate, furthermore alkali metal hydroxides, such as sodium hydroxide and potassium hydroxide, additionally alkali metal alkoxides, such as sodium methoxide and potassium methoxide and sodium ethoxide and potassium ethoxide and also potassium tert.-butoxide, and furthermore lower tertiary alkylamines, cycloalkylamines and aralkylamines, such as, in particular, triethylamine.

Possible diluents for carrying out the process according to the invention are all customary inert organic solvents. Those which can preferably be used are nitriles, such as acetonitrile, furthermore aromatic hydrocarbons, such as benzene, toluene and dichlorobenzene, additionally formamides, such as dimethylformimide, and also strongly polar solvents, such as dimethyl sulphoxide and hexamethylphosphoramide.

The reaction temperatures can be varied within a relatively wide range when carrying out the process according to the invention. In general, the reaction is carried out at temperatures between 0° C. and 200° C., preferably between 50° C. and 150° C.

When carrying out the process according to the invention, 1 to 4 moles of azole of the formula (III) and 1 to 2 moles of base are preferably employed per mole of oxirane of the formula (II). The final products are isolated in a customary member.

The triazolylmethyl-cyclopropyl derivatives of the formula (I) according to the invention can be converted into acid addition salts or metal salt complexes.

In order to prepare acid addition salts of the compounds of the formula (I), suitable acids are preferably those which have already been mentioned as preferred acids in connection with the description of the acid addition salts according to the invention.

The acid addition salts of the compounds of the formula (I) can be obtained in a simple manner by customary salt-formation methods, for example by dissolving a compound of the formula (I) in a suitable inert solvent and adding the acid, for example hydrochloric acid, and can be isolated in a known manner, for example by filtering off, and, if desired, can be purified by washing with an inert organic solvent.

In order to prepare metal salt complexes of the compounds of the formula (I), suitable salts of metals are preferably those which have already been mentioned as preferred metal salts in connection with the description of the metal salt complexes according to the invention.

The metal salt complexes of the compounds of the formula (I) can be obtained in a simple manner by customary processes, thus, for example, by dissolving the metal salt in an alcohol, for example ethanol, and adding to compounds of the formula (I). Metal salt complexes can be purified in a known manner, for example by filtering off, isolating and, if desired, by recrystallizing.

The active compounds according to the invention have a strong microbicidal action and can be employed as fungicides.

Fungicides are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as *Septoria modorum;* Leptosphaeria species, such as *Leptosphaeria modorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combatting *Pyricularia oryzae* and *Pellicularia sasakii* on rice and for combatting cereal diseases, such as *Leptosphaeria nodorum,* Erysiphe and Pseudocercosporella. In addition, the substances according to the invention show very good action against Venturia, Sphaerotheca and Botrytis. Furthermore, the substances according to the invention also show a very good in-vitro action.

Finally, the substances according to the invention also exert a herbicidal action against grasses.

The substances according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic materials, such as highly-disperse silica, alumina and silicates. As solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, molybdenum and zinc.

The formulations in general contain between 0.1 and 95 per cent by weight of active compound, preferably between 0.5 and 90%.

The active compounds according to the invention can be present in the formulations as a mixture with other known active compounds, such fungicides, insecticides, acaricides and herbicides, as well as in mixtures with fertilizes and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting foaming, brushing on and the like. It is furthermore possible to apply the active compounds by the ultra-low volume method or to inject the active compound formulation or the active compound itself into the soil. The seeds of the plants can also be treated.

When using the substances according to the invention, the application rate can be varied within a relatively wide range depending on the manner of application. Thus, in the treatment of parts of plants, the active compound concentrations in the use forms are in general between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and the use of the substances according to the invention can be seen from the following examples.

PREPARATION EXAMPLES

EXAMPLE 1

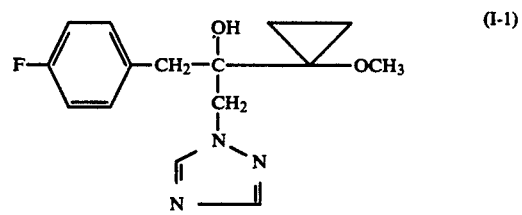
(I-1)

A mixture of 1.5 g (6.8 mmol) of 2-(4-fluorobenzyl)-2-(1-methoxy-cyclopropyl)-oxirane, 1.5 g (21.7 mmol) of 1,2,4-triazole and 0.2 g (1.8 mmol) of potassium tert.-butoxide in 10 ml of absolute dimethylformamide is heated at 80° C. under a nitrogen atmosphere for 8 hours. The solvent is then stripped off under reduced pressure and the residue remaining is dissolved in ethyl acetate. The organic solution is washed with water, dried over sodium sulphate and concentrated under reduced pressure. The residue is chromatographed on silica gel using dichloromethane as the eluent. After evaporating the eluate, 0.45 g (23% of theory) of 1-(4-fluoro-phenyl)-2-(1-methoxy-cyclopropyl)-3-(1,2,4-triazol-1-yl)-propan-2-ol is obtained in the form of a solid substance of melting point 72° C.

Preparation of starting substances

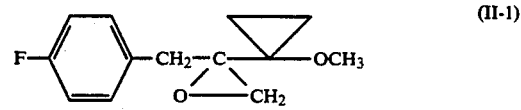
(II-1)

15 ml of absolute dimethyl sulphoxide are added dropwise at 10° C. under a nitrogen atmosphere to a mixture of 2.2 g (10 mmol) of trimehylsulphoxonium iodide and 0.4 g (13 mmol) of sodium hydride (80% pure). After addition is complete, the mixture is allowed to warm to room temperature in the course of 10 minutes and a solution of 2 g (9.6 mmol) of 4-fluorobenzyl 1-methoxycyclopropyl ketone in 10 ml of absolute dimethyl sulphoxide is then added dropwise with stirring. The reaction mixture is then poured into water. The resulting mixture is extracted with ethyl acetate. The combined organic phases are washed with water, dried over sodium sulphate and concentrated by stripping off the solvent under reduced pressure. 1.5 g (70% of theory) of 2-(4-fluoro-benzyl)-2-(1-methoxy-cyclopropyl)-oxirane are obtained in this manner in the form of an oil.

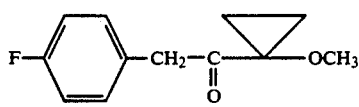
(IV-1)

2.7 g (18.7 mmol) of 4-fluoro-benzyl chloride are added dropwise to a mixture of 0.45 g (18.5 mmol) of magnesium turnings and 15 ml of absolute ether in such a way that the ether boils gently. The reaction mixture is subsequently stirred under reflux for 30 minutes and then cooled to −78° C. 2 g (12.6 mmol) of N-methoxy-N-methyl-1-methoxycyclopropane-carboxamide are then added dropwise at −78° C. with stirring and the mixture is then allowed to warm to room temperature. The reaction mixture is stirred at room temperature for the further 2 hours and then poured into dilute aqueous hydrochloric acid. The resulting mixture is extracted with ether, and the combined organic phases are washed with water, dried over sodium sulphate and concentrated by stripping off the solvent under reduced pressure. 2.3 g (88% of theory) of 4-fluorobenzyl 1-methoxycyclopropyl ketone remain in the form of an oil.

$^1$H NMR (200 MHz, CDCl$_3$): δ=1.1–1.33 (m, 4H); 3.38 (s, 3H); 3.97 (s, 2H); 6.92–7.15 (m, 2H); 7.15–7.25 (m, 2H).

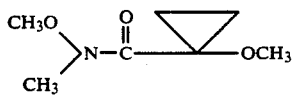
(VII)

10 g (74 mmol) of 1-methoxy-cyclopropane-carbonyl chloride are added at 20° C. with stirring to a mixture of 8 g (82 mmol) of N,O-dimethyl-hydroxylamine hydrochloride and 100 ml of absolute dichloromethane. 13 g (164 mmol) of absolute pyridine are then added dropwise at 0° C. The mixture is initially subsequently stirred at 20° C. for one hour and then at 40° C. for one hour, the precipitate is then filtered off and 100 ml of dichloromethane are added. The reaction mixture is washed with water, dried over sodium sulphate and concentrated by stripping off the solvent under reduced pressure. The remaining residue is subjected to a vacuum distillation. 10 g (85% of theory) of N-methoxy-N-methyl-1-methoxy-cyclopropanecarboxamide are obtained in this manner in the form of an oil having a boiling point of b.p.=125° C. at 20 mbar.

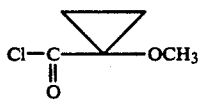
(X)

68 ml (0.78 mol) of thionyl chloride are added dropwise at room temperature to a suspension of 61 g (0.52 mol) of 1-methoxy-cyclopropane-carboxylic acid in 200 ml of dichloromethane. The reaction mixture is heated under reflux for two hours, then cooled and concentrated by stripping off the volatile constituents under reduced pressure. The remaining residue is distilled in a water jet vacuum. 51.2 g (72% of theory) of 1-methoxy-cyclopropane-carbonyl chloride are obtained in this manner in the form of a liquid having a boiling point of 47° C. at 18 mbar.

IR spectrum: band at 1,780 cm$^{-1}$.

EXAMPLE 2

(I-2)

A solution of 5.4 g (0.024 mol) of 2-(1-methoxycyclopropyl)-2-(4-chlorophenyl)-oxirane in 20 ml of dimethylformamide is added dropwise with stirring to a solution of 6.6 g (0.096 mol) of 1,2,4-triazole and 1.0 g (0.0096 mol) of potassium tert.-butoxide in 50 ml of dimethylformamide warmed to 80° C. The reaction mixture is stirred at 80° C. for 12 hours, then cooled to room temperature and concentrated under reduced pressure. The residue which remains is dissolved in ethyl acetate, and the resulting organic solution is washed three times with water, dried over sodium sulphate and concentrated by stripping off the solvent under reduced pressure. The residue is chromatographed on silica gel using a mixture of cyclohexane/ethyl acetate=1:1 as the eluent. After evaporating the eluate, 3.4 g (48% of theory) of 2-(4-chloro-phenyl)-2-(1-methoxycyclopropyl)-1-(1,2,4-triazol-1-yl)-ethan-2-ol are obtained in the form of a solid substance having a melting point of 106° C.

$^1$H NMR (250 MHz, CDCl$_3$): δ=1.40–1.080 (m, 4H); 2.93 (s, 3H); 4.80 (2H, AB system); 7.30 and 7.50 (2H, AB system); 7.82 (s, 1H); 8.08 (s, 1H).

Preparation of starting substances (II-1)

A suspension of 0.82 g (0.0342 mol) of sodium hydride, 7.5 g (0.0342 mol) of trimethylsulphoxonium iodide and 50 ml of dimethyl sulphoxide is initially stirred at room temperature for 30 minutes and then a solution of 6.0 g (0.0285 mol) of 1-methoxy-cyclopropyl 4-chlorophenyl ketone in 10 ml of dimethyl sulphoxide is added at 10° C. After addition is complete, the mixture is warmed to room temperature and stirred for a further 3 hours. 10 ml of ethyl acetate are then added to the reaction mixture and it is stirred for a further 5 minutes. The reaction mixture is poured into ice-water, the resulting mixture is extracted three times with cyclohexane, and the combined organic phases are dried over sodium sulphate and concentrated by stripping off the solvent under reduced pressure. 5.4 g (84% of theory) of 2-(1-methoxy-cyclopropyl)-2-(4-chlorophenyl)-oxirane are obtained in this manner and reacted further without additional purification.

(IV-2)

22 ml (0.036 mol) of a 1.6 molar n-butyl-lithium solution are added at −78° C. with stirring to a mixture of 6.9 g (0.036 mol) of 4-bromochlorobenzene and 70 ml of diethyl ether. The reaction mixture is warmed to 0° C. and stirred at this temperature for 15 minutes. After cooling to −78° C. again, a solution of 4.8 g (0.03 mol) of N-methoxy-N-methyl-1-methoxycyclopropane-carboxamide in 20 ml of diethyl ether is added rapidly. The mixture is then subsequently stirred at −78° C., at 0° C. and at room temperature, in each case for one hour. 20 ml of ethyl acetate are then added to the reaction mixture, which is stirred for 5 minutes and then poured into ice-water. The resulting mixture is extracted three times with ethyl acetate, and the combined organic phases are dried over sodium sulphate and then concentrated by stripping off the solvent under reduced pressure. 6.1 g (97% of theory) of 1-methycyclopropyl 4-chlorophenyl ketone are obtained in this manner and are reacted further without prior purification.

$^1$H NMR (250 MHz, CDCl$_3$): δ=1.1–1.5 (m, 4H); 3.17 (s, 3H); 7.42 and 8.08 (2H, AB system).

The substances shown in the following examples are also prepared by the methods indicated in the prior examples.

EXAMPLE 3

(I-3)

Melting point: 107°–108° C.

EXAMPLE 4

(I-4)

IR spectrum: Bands at 1595 cm$^{-1}$, 1700 cm$^{-1}$ and 3100–3400 cm$^{-1}$.

The compounds indicated below are employed as comparison substances in the following Use Examples:

= (A)

= (B)

= (C)

= (D)

The compounds are disclosed in EP-OS (European Published Specification) 0,180,136.

EXAMPLE A

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (I-2) and (I-4) according to the invention show a substantially better activity than the comparison substances (A) and (B).

EXAMPLE B

Leptosphaeria nodorum test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, compound (I-1) according to the invention shows a substantially better activity than the comparison substance (C).

EXAMPLE C

*Pseudocercosporella herpotrichoides* test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated at the base of the stem with spores of *Pseudocercosporella herpotrichoides.*

The plants are placed in a greenhouse at a temperature of about 10° C. and a relative atmospheric humidity of about 80%.

Evaluation is carried out 21 days after the inoculation.

In this test, compound (I-3) according to the invention shows a substantially better activity than the comparison substance (D).

It is understood that the specification and examples are illustrative but not limitative of the present invention and that other embodiments within the spirit and scope of the invention will suggest themselves to those skilled in the art.

We claim:

1. A compound selected from the group consisting of
2-(4-chloro-phenyl)-2-(1-methoxycyclopropyl)-1-(1,2,4-triazol-1-yl)-ethan-2-ol,
2-(2,4-difluoro-phenyl)-2-(1-methoxycyclopropyl)-1-(1,2,4-triazol-1-yl)-ethan-2-ol and
1-(α-naphthyl)-1-(1-methoxycyclopropyl)-2-(1,2,4-triazol-1-yl)-ethan-2-ol.

2. A compound according to claim 1, wherein such compound is 2-(4-chloro-phenyl)-2-(1-methoxycyclopropyl)-1-(1,2,4-triazol-1-yl)-ethan-2-ol of the formula

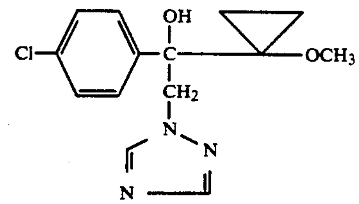

I-2 or an addition product thereof with an acid or metal salt.

3. A compound according to claim 1, wherein such compound is 2-(2,4-difluoro-phenyl)-2-(1-methoxycyclopropyl)-1-(1,2,4-triazol-1-yl)-ethan-2-ol of the formula

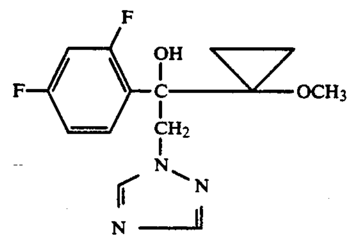

I-3 or an addition product thereof with an acid or metal salt.

4. A compound according to claim 1, wherein such compound is 1-(α-naphthyl)-1-(1-methoxy-cyclopropyl)-2-(1,2,4-triazol-1-yl)-ethan-2-ol of the formula

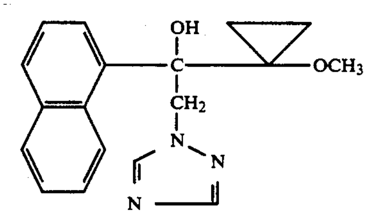

I-4 or an addition product thereof with an acid or metal salt.

5. A fungicidal composition comprising a fungicidally effective amount of a compound or addition product thereof according to claim 1 and an inert diluent.

6. A method of combating fungi which comprises applying to such fungi or to a fungus habitat a fungicidally effective amount of
1-(4-fluoro-phenyl)-2-(1-methoxy-cyclopropyl)-3-(1,2,4-triazol-1-yl)-propan-2ol,
2-(4-chloro-phenyl)-2-(1-methoxycyclopropyl)-1-(1,2,4-triazol-1-yl)-ethan-2-ol,
2-(2,4-difluoro-phenyl)-2-(1-methoxycyclopropyl)-1-(1,2,4-triazol-1-yl)-ethan-2-ol or
1-(α-naphthyl)-1-(1-methoxy-cyclopropyl) 2-(1,2,4-triazol-1-yl)-ethan-2-ol, or an addition product thereof.

* * * * *